United States Patent [19]

Maxwell et al.

[11] Patent Number: 5,344,388

[45] Date of Patent: Sep. 6, 1994

[54] TEXTURED SURFACE PROSTHETIC DEVICE

[76] Inventors: G. Patrick Maxwell, 4416 Gerald Pl., Nashville, Tenn. 37205; Jack Fisher, 5884 Fredricksburg Dr., Nashville, Tenn. 37215; Larry Perry, 3333 Country Ridge Dr., Antioch, Tenn. 37013

[21] Appl. No.: 147,453

[22] Filed: Nov. 5, 1993

Related U.S. Application Data

[63] Continuation of Ser. No. 893,749, Jun. 5, 1992, abandoned, which is a continuation of Ser. No. 694,429, May 1, 1991, abandoned.

[51] Int. Cl.⁵ ............................................. A61F 2/26
[52] U.S. Cl. .................................................. 600/40
[58] Field of Search .................. 623/1, 8; 600/38–41

[56] References Cited

U.S. PATENT DOCUMENTS

| | | | |
|---|---|---|---|
| 4,177,805 | 12/1979 | Tudoriu | 600/40 |
| 4,335,714 | 6/1982 | Edgerton et al. | 600/40 |
| 4,523,584 | 6/1985 | Yachia et al. | 600/38 |
| 4,611,584 | 9/1986 | Finney | 600/40 |
| 4,773,403 | 9/1988 | Daly | 600/40 |
| 5,007,929 | 4/1991 | Quaid | 623/8 |
| 5,011,494 | 4/1991 | von Recum et al. | 623/1 X |

FOREIGN PATENT DOCUMENTS

| | | | |
|---|---|---|---|
| 1024068 | 6/1983 | U.S.S.R. | 600/40 |

*Primary Examiner*—Randall L. Green
*Assistant Examiner*—Mary Beth Jones
*Attorney, Agent, or Firm*—Renner, Otto, Boisselle & Sklar

[57] ABSTRACT

A penile prosthesis device includes at least one elongate member for implantation into the corpus cavernosum of the penis, the elongate member having an outer surface morphology facilitating tissue adherence to the implanted elongate member and tissue ingrowth.

11 Claims, 1 Drawing Sheet

U.S. Patent  Sep. 6, 1994  5,344,388
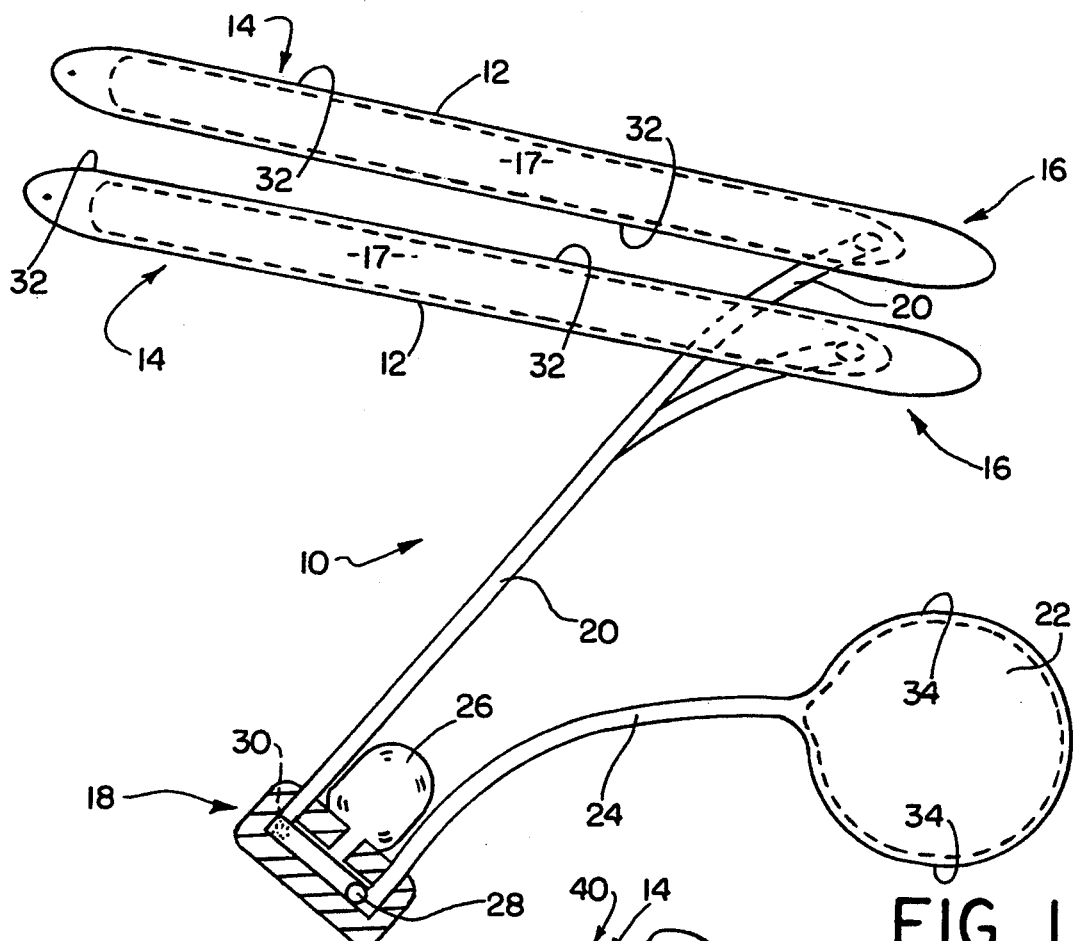
FIG. 1
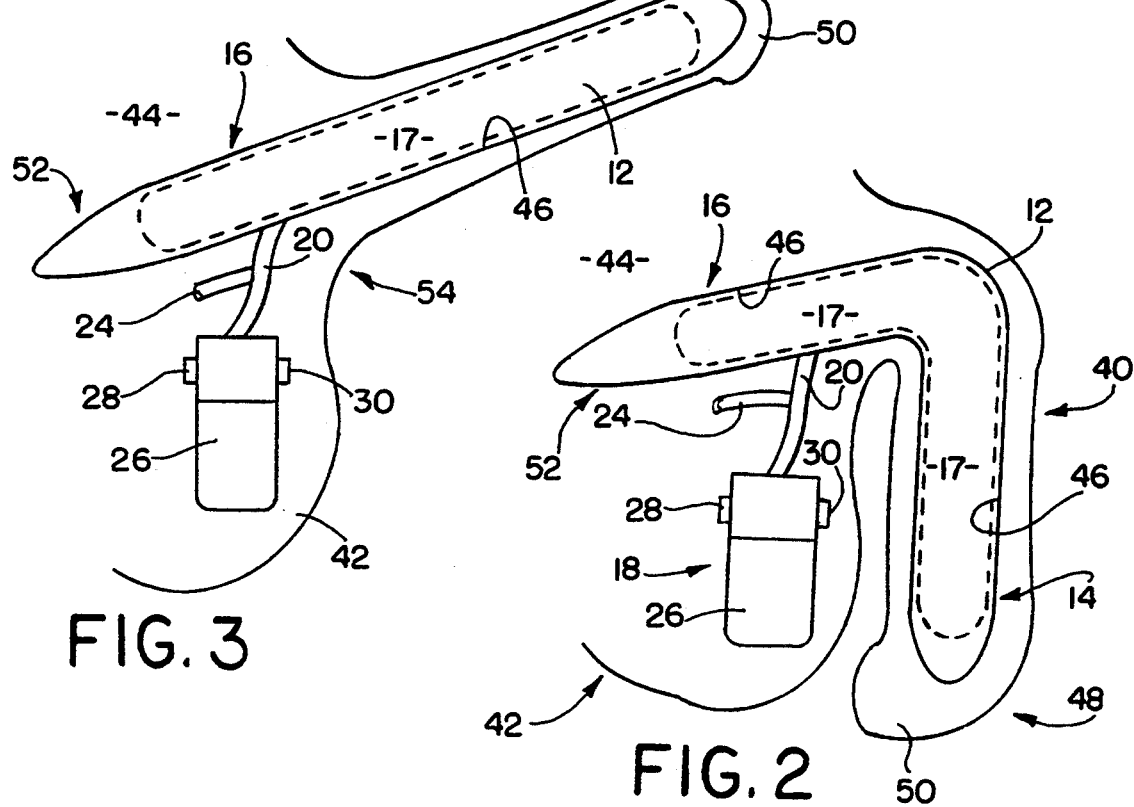
FIG. 3
FIG. 2

TEXTURED SURFACE PROSTHETIC DEVICE

CROSS-REFERENCE TO RELATED APPLICATIONS

This is a continuation of copending application Ser. No. 07/893,749 filed on Jun. 5, 1992, now abandoned, which is a continuation of U.S. patent application Ser. No. 07/694,429, filed May 1, 199 now abandoned.

FIELD OF THE INVENTION

This invention relates generally to an implanted device, particularly to a surgically implanted genitourinary prosthesis device, and more particularly, to a surgically implanted penile prosthesis.

BACKGROUND OF THE INVENTION

It has recently been estimated that as many as ten million men in the United States alone suffer from chronic erectile impotence, or the inability to maintain an erection of sufficient rigidity or duration to engage in coitus. Of that number approximately eighty-five percent of the cases of chronic erectile impotence are believed to be related to organic, rather than psychological, causes. Many of these organically caused cases of impotence, as well as some of the psychologically rooted cases which have not responded to treatment, are candidates for a penile prosthesis device. In fact, the surgical implantation of penile prostheses has become an increasing accepted technique in the treatment of chronic erectile impotence with approximately 35,000 prostheses being implanted each year.

There are several types of penile prostheses currently available. One type, known as a rigid prosthesis, includes a pair of relatively rigid elongate rods which are implanted into the corpus cavernosum bodies of the penis, which are columns of erectile tissue running the length of the penis. The implanted rods maintain the penis in a constant state of erection, which can be difficult to conceal and embarrassing in some situations. Another type, known as a semi-rigid prosthesis, typically consists of bendable, or malleable, rods which when implanted into the penis, maintain the penis in a manipulated position. While these devices allow manipulation into a variety of positions, they always maintain the girth of an erect penis and still do not simulate flaccidity overly well.

A third type of prosthesis, and by far the most mechanically complex, is an inflatable prosthesis. In this type of device inflatable cylinders are implanted in the corpus cavernosum bodies of the penis with a reservoir implanted in the abdominal cavity and a manual pump implanted in the scrotum. However, the locations of the reservoir and pump may vary, with one Model even including all of the components in the corpus cavernosum. When the pump is actuated, fluid from the reservoir inflates and expands the cylinder thus simulating the girth and rigidity of an erect penis. Opening of a valve allows the fluid in the cylinder to return to the reservoir causing the cylinder to deflate, and thus simulating a normally flaccid penis. These are just examples of the many types of prostheses known.

Regardless of the type of protheses or the mechanical complexity, the various devices all require implantation into the penis and possibly also into the abdominal cavity and the scrotum. Where the prostheses comes into contact with surrounding tissue, smooth surface silicone rubber is generally employed as it is nontoxic, nonreactive, and resistant to wear, and also maintains its functionality for an extended period of time. However, other smooth surfaced materials, such as certain plastics, have also been used.

In response to the presence of an implanted foreign object, the body generally reacts by forming a fibrous pseudocapsule of scar tissue around the object. This pseudocapsule of scar tissue ideally acts to support the implanted prosthetic device, allowing it to function without displacement. However, tissue adherence and tissue ingrowth does not occur around and to the surface of an inert smooth surface device. The scar tissue forming the pseudocapsule has a linear collagen arrangement that can contract and displace the implanted device. Also, because tissue adherence to the device does not occur, periprosthetic dead spaces are created and the implanted device may thus move relative to the host tissue inducing cellular trauma and the accompanying risk of infection. Further, the implanted device may erode the surrounding tissue and eventually cause perforation. The uneven formation of the fibrous scar tissue around the device may also cause contracture of various components of the implant, such as the inflatable cylinders, thus reducing their functionality.

Unfortunately, approximately twenty percent of the patients receiving penile prosthetic devices suffer complications such as mechanical failure of the prostheses or those related to erosion, infection, perforation, contracture, uncontrolled mobility of the device and pain. Most often correction of the complication requires removal of the device, treatment of the affected tissue, and eventual replacement of the prosthesis. With the increasing acceptance of penile prostheses, physicians and manufacturers have attempted to reduce the incidents of complication predominately by improving the mechanical reliability of the devices and by using improved infection fighting drugs.

It would be desirable to provide a prosthetic device which reduced the occurrence of complications.

SUMMARY OF THE INVENTION

The present invention provides a penile prosthesis device which reduces the incidents of complication. The device includes a number of components arranged as is typical in a penile prosthetic device with the components contacting body tissue having a surface morphology proximate to the tissue that provides for tissue adherence and tissue ingrowth, and control of scar tissue contracture. The surface morphology is preferably textured and the surface may be an integral part of the device or a covering for individual components of the device.

In accordance with the present invention, a penile prosthesis device includes at least one elongate member for implantation into the corpus cavernosum of the penis, the elongate member having an outer surface morphology facilitating tissue adherence to the implanted elongate member and tissue ingrowth.

In accordance with the another aspect of the invention, an implantable genitourinary device has an outer surface morphology facilitating tissue adherence and tissue ingrowth to the surface of the device.

In accordance with still a further aspect, a penile prosthesis device includes at least one elongate member for implanting into a corpus cavernosum of a penis, the elongate member having a textured outer surface for contact with body tissue.

These and other objects, advantages, features and aspects of the present invention will become apparent as the following description proceeds.

To the accomplishments of the foregoing and related ends, the invention, then comprises the features hereinafter fully described in the specification and particularly pointed out in claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

BRIEF DESCRIPTION OF THE DRAWINGS

In the annexed drawings:

FIG. 1 is an illustration of an inflatable penile prosthesis device including textural surface components in accordance with the present invention;

FIG. 2 is a cross-sectional illustration of a flaccid penis with a typical inflatable prosthetic device in place; and FIG. 3 is a cross-sectional illustration as in FIG. 2 but with the inflatable device in its inflated state.

DETAILED DESCRIPTION OF THE INVENTION

With reference now to the attached drawings in which like reference numerals depict like items, and initially to FIG. 1, there is shown an illustration of an inflatable penile prosthesis 10 in accordance with an embodiment of the present invention. The penile implant 10 discussed is a typical inflatable implant having separate components, such as that manufactured by American Medical Supply, although it will be appreciated that the invention is equally applicable to rigid and semi-rigid rod implants as well as other types of inflatable implants, such as those having a self-contained pump and fluid reservoir, and may also be applicable to other genitourinary implants. The penile prosthesis device 10 includes a pair of flexible, inflatable cylinders 12 each having an inflatable distal portion 14 and a relatively rigid proximal end 16. The interior volumes 17 of the inflatable distal portions 14 are in fluid communication with a pump assembly 18 through fluid lines 20 which is in turn in fluid communication with a reservoir 22 through a fluid line 24. The pump assembly 18 includes a mechanically activated bulb pump 26 for transferring fluid from the reservoir 22 to the inflatable cylinders 12, a relief valve 28 to prevent over-inflation, and a deflation valve 30 to allow fluid in the inflatable distal portions 14 of the inflatable cylinders 12 to be transferred back to the reservoir 22.

While the interior components of the reservoir 22, the pump assembly 18 and the inflatable cylinders 12 may be composed of any suitable material which is nonreactive and nontoxic, the outer components of the prosthetic device 10 in contact with the surrounding body tissue are covered with or otherwise have an outer surface comprised of a nontoxic, nonreactive material preferably having a surface morphology with good tissue adherence and tissue ingrowth characteristics, such as a textured medical grade silicone rubber manufactured by McGhan Medical Corporation under the tradename Biocell. The textured Biocell material has a pore density of approximately 2.4 pores per square millimeter of surface area and pore size distribution ranging from approximately 60 microns to approximately 567 microns with a mean pore size of approximately 263 microns. It is of particular importance that the inflatable cylinders, or rigid or semi-rigid rods of other prostheses, have such a textured outer surface 32 as these components are subject to the most movement and stress. The texturing is formed directly in the outer surface 32 of the elongate members 12 thus constituting an integral part thereof and is left exposed to body tissue when implanted as described hereafter. The textured outer surface 32 completely encloses the elongate members 12 which do not have any openings extending therethrough as shown. Further, it is desirable that the outer surface 34 of the fluid reservoir 22 in contact with body tissue also has a surface morphology with good tissue adherence and tissue ingrowth characteristics to reduce the incidents of penile prosthesis complications. Similarly, many of the other components, such as the pump assembly 18 and the fluid lines 20, 24, may be constructed with a textured surface material also.

FIG. 2 schematically shows a penis 40 with an inflatable penile prosthetic device 10, such as that described above, implanted. The scrotum is shown at 42 and the internal pelvic region is depicted at 44. The penis 40 includes corpus cavernosum bodies 46 which are columns of fibrous erectile tissue forming the dorsum and sides of the penis and thus providing its width and shape. It is into these bodies 46 that the inflatable cylinders 12, or the rigid or semi-rigid rods of other devices, are implanted. Each inflatable cylinder 12 is sized to extend from the root end 52 to the distal end 48 of a corpus cavernosum 46 and substantially to fill the interior of the corpus cavernosum. The pump assembly 18 is disposed in the scrotum 42 and is interconnected with the interior volumes 17 of the inflatable distal portions 14 of the inflatable cylinders 12 through appropriate fluid lines 20. The reservoir 22 is typically located in the abdominal cavity (not shown) and as is stated above is connected to the pump assembly 18 through the fluid line 24.

When the flaccid state of the penis is simulated, as shown in FIG. 2, the inflatable cylinders 12 are at least partially deflated with the reserve fluid stored in the reservoir 22. When an erection is desired, the bulb pump 26 is manually actuated through the scrotum 42. The actuation of the bulb pump 26 forces fluid to flow from the reservoir 22 into the interior volumes 17 of the inflatable distal portions 14 of the inflatable cylinders 12, thus inflating the cylinders. The inflatable cylinders 12, when in their inflated state, become wider and assume a relatively rigid elongate condition, as shown in FIG. 3. The penis 40 is likewise forced into a rigid axial position, thus simulating an erection. To return the inflatable cylinders 12 to their deflated state, and thus the penis 40 to its flaccid condition, the deflation valve 30 is depressed, also through the scrotum 42, allowing the fluid stored in the interior volumes 17 of the distal portions 14 of the inflatable cylinders 12 to return to the reservoir 22.

There are many surgical procedures known for implanting a penile prosthesis as is discussed generally in Urologic Clinics of North America, February, 1989, Volume 16, No. 1, which is incorporated herein by this reference. One typical method generally includes forming a penoscrotal incision, or a cut extending from the scrotum 42 through the base of the penis 40 and partially toward the distal end 48 of the penis, generally indicated in FIG. 3 at 54. The corpus cavernosum bodies 46 are then measured and dilated, and the appropriately sized inflatable cylinders 12 are chosen. Typically, a thread is secured to the distal end 14 of the inflatable cylinder 12 and the thread is fed through the corpus cavernosum to emerge from the glans penis 50. The distal portion 14 of an inflatable cylinder 12 is then fed through the incision 54 in the base of the penis 40 and pushed towards the distal end 48 of a corpus cavernosum 46, Pulling on the thread connected to the distal portion 14 of the cylinder 12 exteriorly of the glans penis 50 thus pulls the inflatable cylinder through the corpus cavernosum 46 until the distal portion 14 reaches the rear of the glans penis. The proximal end 16 of the inflatable cylinder 12 is then inserted into the corpus cavernosum 46 through the incision 54 and is pushed back to the root end 52 of the corpus cavernosum. As the proximal end 16 of an inflatable cylinder 12 is generally solid and relatively rigid, it can easily be forced to the root end 52 of the corpus cavernosum 46 without the need of a guiding thread. The same or a similar process may then be repeated to place a second inflatable cylinder 12 in a separate corpus cavernosum 46. The pump assembly 18 is then inserted in the scrotum 42, the reservoir 22 is positioned in the abdominal cavity and the fluid lines 20, 24 are threaded through the body between the components and the components are suitably interconnected. The incision 54 is then closed.

It has been found, in contrast with a smooth surface, providing the implanted components with a textured surface the texturing of which is formed directly in the outer surface of the implanted components and is left exposed to body tissue has the advantage that as the body heals a more random distribution of collagen deposits is provided over the textured surface with tissue adherence and tissue ingrowth over the increased surface area of the textured surface. Thus, the scar tissue forming adjacent the implanted components will adhere to the outer surfaces of the components having a textured morphology and will form a complete encapsulating enclosure of scar tissue. This is unlike the encapsulating tissue which typically forms around smooth surfaced materials implanted in the body, in that such tissue does not adhere to the smooth surface and often results in periprosthetic dead space and an insufficient encapsulation. Since the scar tissue is able to adhere to the textured surfaces of the components, the tissue will tend to form evenly over the complete surface of the implanted prostheses thus forming a more expandable, compliant, and malleable encapsulation of scar tissue with minimal contracture. Consequently, the textured surface prosthetic device will be adequately supported by the adhered encapsulated tissue, and movement of the prosthetic device relative to the adjacent tissue is significantly reduced. Thus, infection due to cellular trauma, and erosion, perforation, and uncontrolled movement of the device are significantly reduced. Mechanical failure of the device due to contracture may also be reduced.

What is claimed is:

1. A penile prosthesis device capable of repeated circumferential expansion and contraction in use for the correction of erectile impotence, comprising at least one flexible elongate member for implantation into a corpus cavernosum of a penis, said elongate member being constructed substantially of silicone rubber and having a fluid impervious inner surface defining an interior chamber and an outer surface, said outer surface having texturing means formed directly in said outer surface which is left exposed to body tissue to facilitate tissue adherence and tissue ingrowth over substantially the entire implanted elongate member to thereby assure repeated circumferential expansion and contraction by a more expandable, compliant and malleable encapsulation of scar tissue with minimal contracture and to thereby prevent at the same time the formation of periprosthetic dead space about the elongate member so as to significantly reduce infection due to cellular trauma and erosion, perforation and uncontrolled movement of the device wherein said texturing in said outer surface has a pore size distribution ranging from approximately 60 microns to approximately 567 microns.

2. The device of claim 1 wherein said outer surface completely encloses said elongate member.

3. The device of claim 1 wherein there are no openings extending through said outer surface of said elongate member.

4. The device of claim 1 further comprising a fluid reservoir and a fluid pump, said reservoir being in fluid communication with said pump and said pump being in fluid communication with said inflatable elongate member.

5. The device of claim 4 wherein said outer surface has a textured surface morphology for facilitating tissue adherence and tissue ingrowth.

6. The device of claim 1 wherein said texturing in said outer surface has a pore density of approximately 2.4 pores per square millimeter of surface area.

7. The device of claim 1 wherein said texturing in said outer surface has a mean pore size of approximately 263 microns.

8. A penile prosthesis device for the correction of erectile impotence which is capable of repeated circumferential expansion and contraction in use by transfer of fluid from and back to a reservoir means for the storage of the fluid when not in use, comprising at least one repeatedly circumferentially expandable and contractable elongate member constructed substantially of silicone rubber for implantation into a corpus cavernosum of a penis, said elongate member including a fluid impervious inner surface defining an interior chamber for containment of a fluid and an outer surface, reservoir means for the storage of said fluid when such fluid is not in said chamber, and means for controllably expanding and contracting said elongate member including pump means for pumping said fluid from said reservoir means into said chamber to circumferentially expand said elongate member, and said elongate member having an outer surface with texturing means over substantially its entire surface, said texturing means being formed directly in said outer surface which is left exposed to body tissue to facilitate formation of an expandable capsule of tissue around said elongate member to thereby assure a more expandable compliant and malleable encapsulation with minimal contracture and to thereby prevent at the same time the formation of periprosthetic dead space about said elongate member so as to significantly reduce infection due to cellular trauma and erosion, perforation and uncontrolled movement of the device wherein said texturing in said outer surface has a pore size distribution ranging from approximately 60 microns to approximately 567 microns.

9. A penile prosthesis device for the correction of erectile impotence which is capable of repeated circumferential expansion and contraction, comprising at least one elongate member for implantation into a corpus cavernosum of a penis, said elongate member being constructed substantially of silicone rubber and having an outer surface with texturing means over substantially its entire surface area, said texturing means being formed directly in said outer surface which is left exposed to body tissue to facilitate tissue adherence and tissue ingrowth over substantially the entire implanted elongate member to thereby assure repeated circumferential expansion and contraction by a more expandable compliant and malleable encapsulation with minimal contraction and to thereby prevent at the same time the formation of periprosthetic dead space about the elongate member so as to significantly reduce infection due to cellular trauma and erosion, perforation and uncontrolled movement of the device wherein said texturing in said outer surface has a pore size distribution ranging from approximately 60 microns to approximately 567 microns.

10. The device of claim 9 wherein said outer surface completely encloses said elongate member.

11. The device of claim 9 wherein there are no openings extending through said outer surface of said elongate member.

* * * * *